United States Patent
Keidar et al.

(10) Patent No.: US 8,287,591 B2
(45) Date of Patent: Oct. 16, 2012

(54) TRANSFORMABLE ANNULOPLASTY RING CONFIGURED TO RECEIVE A PERCUTANEOUS PROSTHETIC HEART VALVE IMPLANTATION

(75) Inventors: Yaron Keidar, Haifa (IL); Mark Konno, Laguna Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 347 days.

(21) Appl. No.: 12/234,580

(22) Filed: Sep. 19, 2008

(65) Prior Publication Data

US 2010/0076549 A1    Mar. 25, 2010

(51) Int. Cl.
*A61F 2/24* (2006.01)
(52) U.S. Cl. ........................ 623/2.36; 623/2.37
(58) Field of Classification Search .................. 623/2.1, 623/2.12, 2.11, 2.36, 2.37, 2.38
See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,164,046 A | 8/1979 | Cooley |
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 6,102,945 A | 8/2000 | Campbell |
| 6,143,024 A | 11/2000 | Campbell et al. |
| 6,159,240 A | 12/2000 | Sparer et al. |

(Continued)

FOREIGN PATENT DOCUMENTS

EP    0 338 994    10/1989

(Continued)

OTHER PUBLICATIONS

PCT International Search Report for PCT App. No. PCT/US2009/057724 (PCT equivalent of U.S. Appl. No. 12/234,580); Apr. 13, 2010.

(Continued)

*Primary Examiner* — David Isabella
*Assistant Examiner* — Randy Shay
(74) *Attorney, Agent, or Firm* — Richard B. Cates

(57) ABSTRACT

The invention is an annuloplasty ring, and associated methods therefore, configured to reshape a native heart valve annulus to correct heart valve function, and also configured to be reshaped into a generally circular form in order to receive and/or support a prosthetic heart valve. The annuloplasty ring may be configured to have a generally D-shaped configuration when initially implanted to correct native valve function, but to assume a generally circular form when subjected to an outward force such as that provided by a dilation balloon.

18 Claims, 10 Drawing Sheets

U.S. PATENT DOCUMENTS

| | | | |
|---|---|---|---|
| 6,183,512 B1 | 2/2001 | Howanec, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,250,308 B1 | 6/2001 | Cox | |
| 6,258,122 B1 | 7/2001 | Tweden et al. | |
| 6,332,893 B1 | 12/2001 | Mortier et al. | |
| 6,348,068 B1 | 2/2002 | Campbell et al. | |
| 6,391,054 B2 | 5/2002 | Carpentier et al. | |
| 6,406,493 B1 | 6/2002 | Tu et al. | |
| 6,419,696 B1 | 7/2002 | Ortiz et al. | |
| 6,602,288 B1 | 8/2003 | Cosgrove et al. | |
| 6,602,289 B1 | 8/2003 | Colvin et al. | |
| 6,619,291 B2 | 9/2003 | Hlavka et al. | |
| 6,709,456 B2 | 3/2004 | Langberg et al. | |
| 6,718,985 B2 | 4/2004 | Hlavka et al. | |
| 6,719,786 B2 | 4/2004 | Ryan et al. | |
| 6,726,717 B2 | 4/2004 | Alfieri et al. | |
| 6,764,510 B2 | 7/2004 | Vidlund et al. | |
| 6,797,002 B2 | 9/2004 | Spence et al. | |
| 6,800,090 B2 | 10/2004 | Alferness et al. | |
| 6,802,860 B2 | 10/2004 | Cosgrove et al. | |
| 6,805,710 B2 | 10/2004 | Bolling et al. | |
| 6,805,711 B2 | 10/2004 | Quijano et al. | |
| 6,858,039 B2 | 2/2005 | McCarthy | |
| 6,918,917 B1 | 7/2005 | Nguyen et al. | |
| 6,921,407 B2 | 7/2005 | Nguyen et al. | |
| 6,942,694 B2 | 9/2005 | Liddicoat et al. | |
| 6,955,689 B2 | 10/2005 | Ryan et al. | |
| 6,966,924 B2 | 11/2005 | Holmberg | |
| 6,986,775 B2 | 1/2006 | Morales et al. | |
| 7,101,395 B2 | 9/2006 | Tremulis et al. | |
| 7,118,595 B2 | 10/2006 | Ryan et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,276,084 B2 | 10/2007 | Yang | |
| 7,294,148 B2 | 11/2007 | McCarthy | |
| 7,381,218 B2 | 6/2008 | Schreck | |
| 7,393,360 B2 | 7/2008 | Spenser et al. | |
| 7,452,376 B2 * | 11/2008 | Lim et al. | 623/2.36 |
| 7,462,191 B2 | 12/2008 | Spenser et al. | |
| 7,510,575 B2 | 3/2009 | Spenser et al. | |
| 7,534,261 B2 | 5/2009 | Friedman | |
| 7,585,321 B2 | 9/2009 | Cribier | |
| 7,625,403 B2 | 12/2009 | Kruvuchko | |
| 7,780,723 B2 | 8/2010 | Taylor | |
| 2001/0021874 A1 * | 9/2001 | Carpentier et al. | 623/2.37 |
| 2002/0062150 A1 | 5/2002 | Campbell et al. | |
| 2003/0033009 A1 | 2/2003 | Gabbay | |
| 2003/0040793 A1 | 2/2003 | Marquez | |
| 2004/0249452 A1 | 12/2004 | Adams et al. | |
| 2004/0249453 A1 | 12/2004 | Cartledge et al. | |
| 2005/0096739 A1 | 5/2005 | Cao | |
| 2005/0131533 A1 | 6/2005 | Alfieri et al. | |
| 2005/0251251 A1 | 11/2005 | Cribier | |
| 2005/0256567 A1 | 11/2005 | Lim et al. | |
| 2005/0256568 A1 | 11/2005 | Lim et al. | |
| 2005/0267572 A1 | 12/2005 | Schoon et al. | |
| 2005/0278022 A1 | 12/2005 | Lim | |
| 2006/0015178 A1 | 1/2006 | Moaddeb et al. | |
| 2006/0015179 A1 | 1/2006 | Bulman-Fleming et al. | |
| 2006/0020336 A1 | 1/2006 | Liddicoat | |
| 2006/0025858 A1 | 2/2006 | Alameddine | |
| 2006/0030885 A1 | 2/2006 | Hyde | |
| 2007/0016287 A1 * | 1/2007 | Cartledge et al. | 623/2.11 |
| 2007/0067029 A1 * | 3/2007 | Gabbay | 623/2.13 |
| 2007/0100441 A1 | 5/2007 | Kron et al. | |
| 2007/0162111 A1 | 7/2007 | Fukamachi et al. | |
| 2008/0027483 A1 * | 1/2008 | Cartledge et al. | 606/201 |
| 2008/0161910 A1 | 7/2008 | Revuelta | |
| 2008/0161911 A1 | 7/2008 | Revuelta | |
| 2008/0183273 A1 * | 7/2008 | Mesana et al. | 623/1.11 |
| 2008/0200980 A1 * | 8/2008 | Robin et al. | 623/2.11 |
| 2008/0208329 A1 * | 8/2008 | Bishop et al. | 623/2.11 |
| 2008/0215144 A1 | 9/2008 | Ryan et al. | |
| 2008/0269878 A1 | 10/2008 | Iobbi | |
| 2008/0275549 A1 | 11/2008 | Rowe | |
| 2009/0005863 A1 * | 1/2009 | Goetz et al. | 623/2.18 |
| 2009/0082857 A1 * | 3/2009 | Lashinski et al. | 623/2.18 |
| 2009/0093876 A1 | 4/2009 | Nitzan | |
| 2009/0192602 A1 | 7/2009 | Kuehn | |
| 2009/0192603 A1 | 7/2009 | Ryan | |
| 2009/0192604 A1 | 7/2009 | Gloss | |
| 2009/0192606 A1 | 7/2009 | Gloss et al. | |
| 2009/0216322 A1 * | 8/2009 | Le et al. | 623/2.37 |
| 2010/0076548 A1 * | 3/2010 | Konno | 623/2.1 |
| 2010/0076549 A1 * | 3/2010 | Keidar et al. | 623/2.36 |

FOREIGN PATENT DOCUMENTS

EP    1 034 753    9/2000

OTHER PUBLICATIONS

PCT Written Opinion of the International Searching Authority for PCT App. No. PCT/US2009/057724 (PCT equivalent of U.S. Appl. No. 12/234,580); Apr. 13, 2010.

* cited by examiner

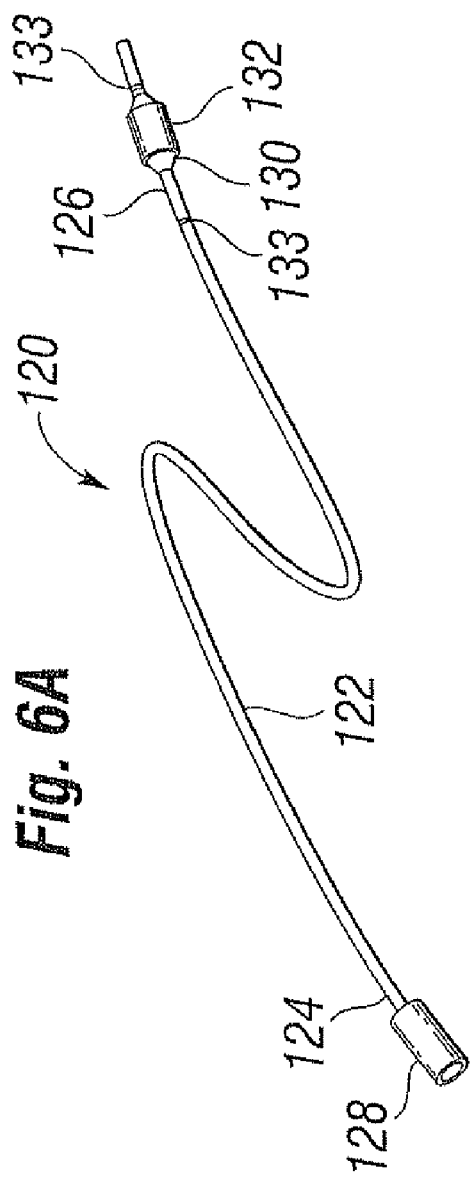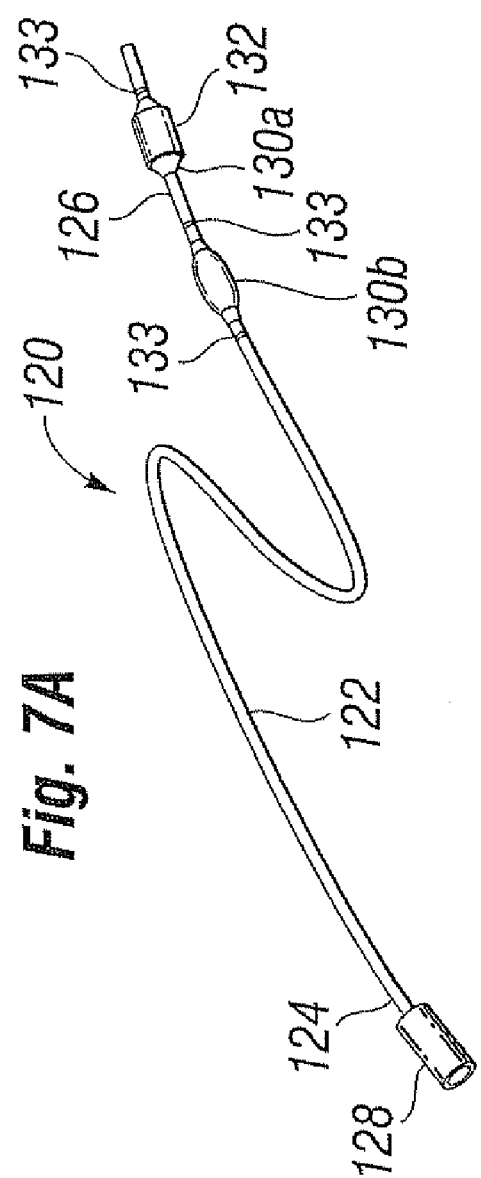

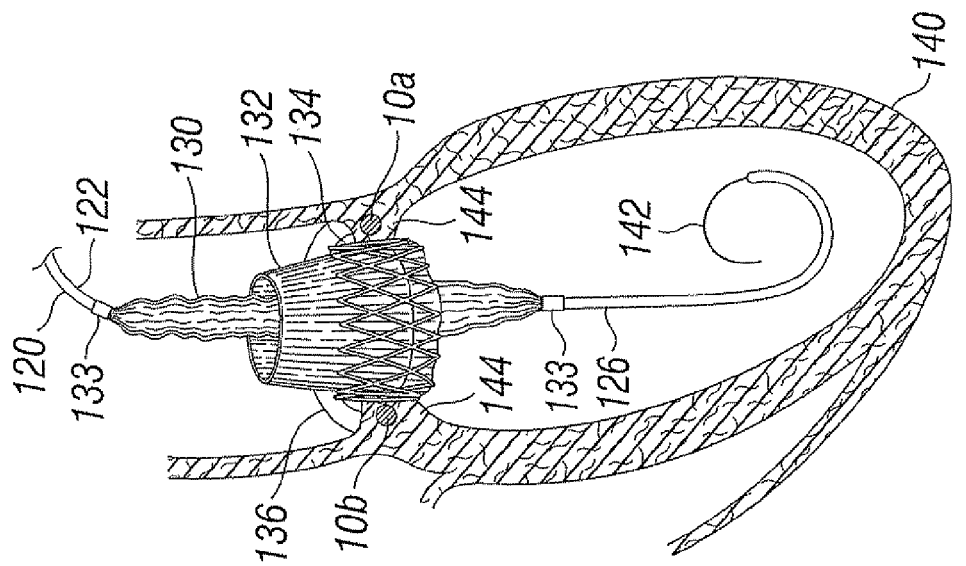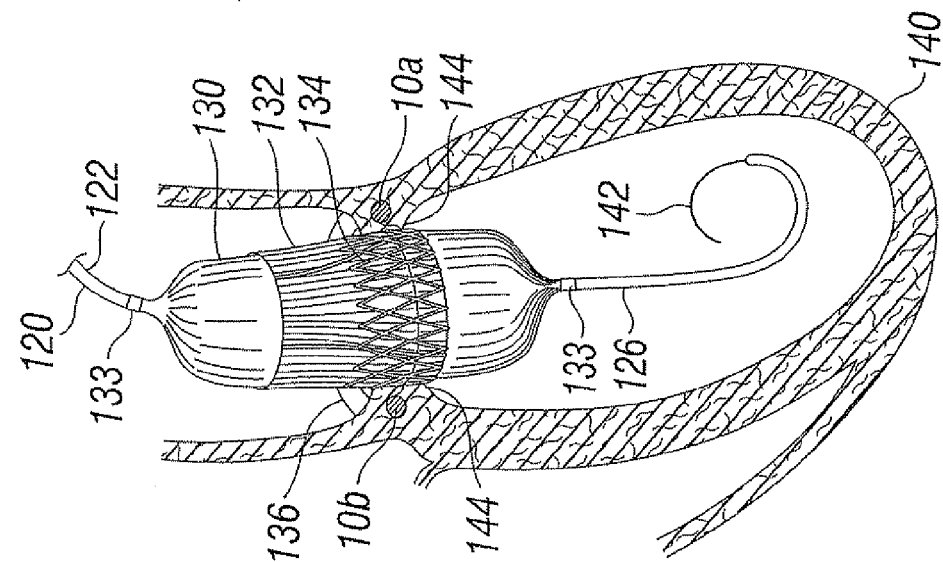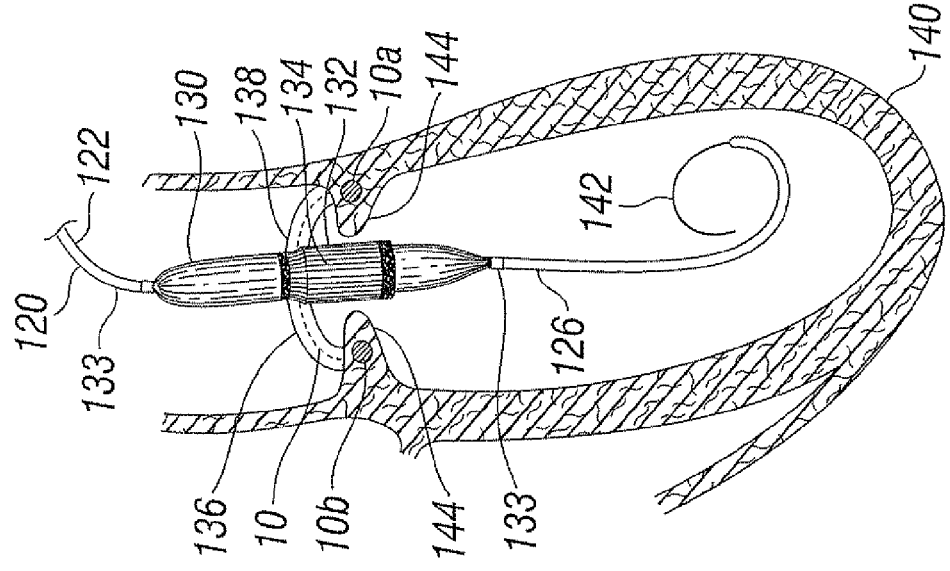

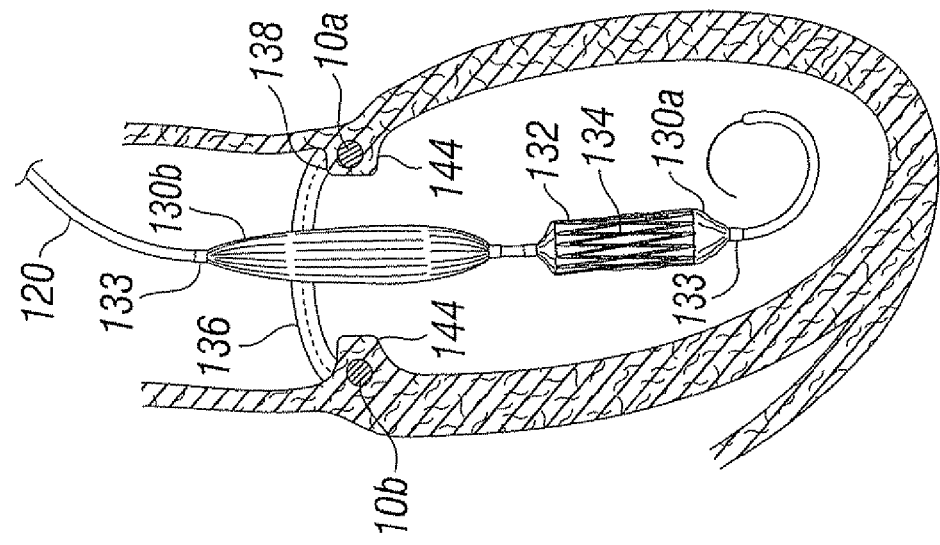
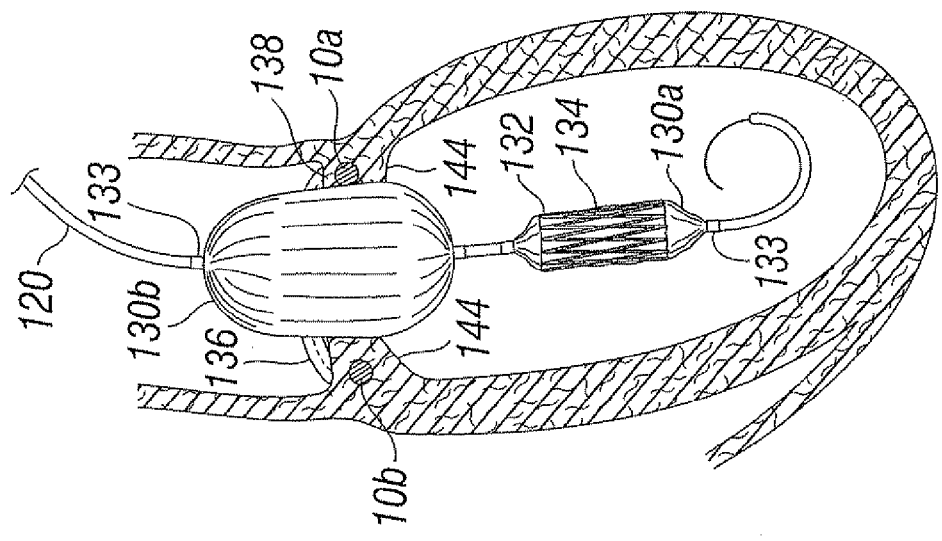
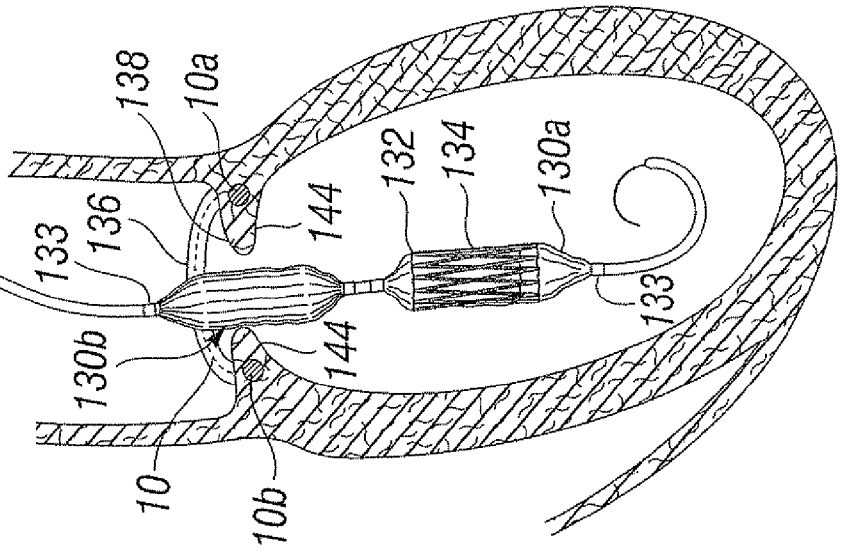

TRANSFORMABLE ANNULOPLASTY RING CONFIGURED TO RECEIVE A PERCUTANEOUS PROSTHETIC HEART VALVE IMPLANTATION

FIELD OF THE INVENTION

The present invention relates to a prosthetic annuloplasty ring for a heart valve, and more particularly to a prosthetic annuloplasty ring configured to receive a prosthetic heart valve therein.

BACKGROUND OF THE INVENTION

In humans and other vertebrate animals, the heart is hollow muscular organ having four pumping chambers separated by four heart valves: aortic, mitral (or bicuspid), tricuspid, and pulmonary. The valves open and close in response to a pressure gradient during each cardiac cycle of relaxation and contraction to control the flow of blood to a particular region of the heart and/or to blood vessels (pulmonary aorta, etc.)

These valves are comprised of a dense fibrous ring known as the annulus, and leaflets or cusps attached to the annulus. For some valves, there is also a complex of chordae tendinae and papillary muscles securing the leaflets. The size of the leaflets or cusps is such that when the heart contracts the resulting increased blood pressure formed within heart chamber forces the leaflets open to allow flow from the heart chamber. As the pressure in the heart chamber subsides, the pressure in the subsequent chamber or blood vessel becomes dominant, and presses back against the leaflets. As a result, the leaflets or cusps come in apposition to each other, thereby closing the passage.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Various surgical techniques may be used to repair a diseased or damaged valve. In a traditional valve replacement operation, the damaged leaflets are typically excised and the annulus sculpted to receive a replacement prosthetic valve.

In many patients who suffer from dysfunction of the mitral and/or tricuspid valves(s) of the heart, surgical repair of the valve (i.e., "valvuloplasty") is a desirable alternative to valve replacement. Remodeling of the valve annulus (i.e., "annuloplasty") is central to many reconstructive valvuloplasty procedures. In 1968, Dr. Alain Carpentier published studies which demonstrated that such remodeling of the valve annulus might be accomplished by implantation of a prosthetic ring (i.e. "annuloplasty ring") to stabilize the annulus and to correct or prevent valvular insufficiency that may result from defect dysfunction of the valve annulus. The annuloplasty ring is designed to support the functional changes that occur during the cardiac cycle: maintaining coaptation and valve integrity to prevent reverse flow while permitting good hemodynamics during forward flow. Annuloplasty procedures are performed not only to repair damaged or diseased annuli, but also in conjunction with other procedures, such as leaflet repair.

The annuloplasty ring typically comprises an inner substrate of a metal such as stainless or titanium, or a flexible material such as silicone rubber or Dacron cordage, covered with a biocompatible fabric or cloth to allow the ring to be sutured to the heart tissue. Annuloplasty rings may be stiff or flexible, may be split or continuous, and may have a variety of shapes, including circular, D-shaped (including kidney-shaped), or C-shaped. Examples are seen in U.S. Pat. Nos. 4,042,979; 4,290,151; 4,489,446; 4,602,911; 5,041,130; 5,061,277; 5,104,407; 5,201,880; 5,258,021; 5,607,471; and 6,187,040, the contents of each of which is hereby incorporated by reference in its entirety.

For some patients, the condition of the native heart valve requires complete replacement using a prosthetic heart valve. Prosthetic heart valves have been known for some time, and have been successfully implanted using traditional open-chest surgical approaches. Sometimes the need for complete valve replacement may arise after a patient has already had a repair using an annuloplasty ring. For example, a native heart valve that was successfully repaired using an annuloplasty ring may suffer further damage years after the annuloplasty ring was implanted.

Implanting a prosthetic heart valve into a patient with a previously-implanted annuloplasty ring typically involves additional steps from a similar procedure in a patient with no annuloplasty ring. Implanting the prosthetic heart valve directly within a previously-implanted annuloplasty ring is generally impractical, largely because most prosthetic heart valves have a generally circular shape whereas most annuloplasty rings are generally non-circular (including "D" and dog-bone shapes). Implanting a prosthetic heart valve in a patient who previously had an annuloplasty ring generally requires the annuloplasty ring to be removed during the same procedure in which the prosthetic heart valve is implanted. In such cases, a surgeon can use a traditional surgical approach to install the prosthetic valve, which can involve the surgeon cutting out the native valve as well as the previously-implanted annuloplasty ring from the heart valve annulus, and then implanting the prosthetic valve into the heart valve annulus.

Percutaneous heart valve replacement has been developed recently, wherein a prosthetic heart valve is advanced percutaneously (e.g., via the femoral artery or other desired approaches) into the heart valve annulus, and then expanded within the heart valve annulus. Percutaneous heart valve replacement is often performed without cutting out the native heart valve, wherein the prosthetic heart valve is expanded in the native heart valve annulus and the native valves are pressed against the valve annulus walls by the expanded prosthetic heart valve. However, in cases where a previously-implanted annuloplasty ring is present, deploying a prosthetic heart valve within the native heart valve may be impractical. The general non-circular shape of the annuloplasty ring may not be compatible with the (typically) circular configuration of the percutaneous prosthetic heart valve, and the annuloplasty ring shape and structure may interfere with the proper placement, deployment, and functioning of the prosthetic heart valve.

Although some of the annuloplasty rings of the prior art have incorporated means for adjusting the shape and size of the ring at the time of implantation, the inventors are aware of no prior art annuloplasty ring constructed and equipped for post-implantation shape change to accommodate and even assist implantation of an expandable heart valve within the heart valve annulus and annuloplasty ring. There is thus a need for an annuloplasty prosthesis and implantation device which will properly reshape/repair a damaged heart valve, but will also enable a prosthetic heart valve to be deployed therein at a later time. The current invention meets this need.

SUMMARY OF THE INVENTION

The invention is an annuloplasty ring configured to receive a prosthetic heart valve, such as a catheter-deployed (transcatheter) prosthetic heart valve, therein. In one embodiment, the annuloplasty ring has a generally non-circular shape when deployed in the patient's native heart valve to correct heart valve function, but is configured to assume a generally circular configuration when subjected to a dilation force such as that provided by a dilation balloon used to deploy a prosthetic valve. The annuloplasty ring can be deployed using various surgical techniques (e.g., traditional open-chest, minimally-invasive, percutaneous, etc.) to correct heart valve function, and the prosthetic valve can be deployed within the same native valve at a much later time. The annuloplasty ring is configured to accept and even improve deployment of the prosthetic valve within the native valve annulus.

In an embodiment of the invention, the annuloplasty ring defines a first inner orifice area when deployed in the patient's native heart valve to correct heart valve function, but is configured to define a second inner orifice area when subjected to a dilation force such as that provided by a dilation balloon used to deploy a prosthetic valve, with the second (dilated) orifice area being larger than the first (pre-dilation) orifice area. In an annuloplasty ring which is generally circular both before and after dilation, the first inner orifice area has a corresponding first inner diameter, and the second inner orifice area has a corresponding second inner diameter, with the second (post-dilation) inner diameter being larger than the first (pre-dilation) inner diameter.

In one embodiment, the annuloplasty ring has a generally curved portion and a generally straight portion, with the generally curved portion being generally rigid and the generally straight portion being generally flexible. The annuloplasty ring may form a continuous loop or a dis-continuous loop, and/or may be generally "D"-shaped (including kidney shapes) or otherwise generally non-circular. The ring may include upward and/or downward structures, such as bows, when viewed from the side.

In an embodiment of the invention, an annuloplasty ring is a discontinuous structure having a generally rigid curved portion and two generally straight portions extending therefrom, with the generally straight portions aligned with each other to form a generally straight (but discontinuous) structure.

An embodiment of the invention includes a first generally rigid section, a second generally rigid section, and a restraint configured to prevent movement of the first generally rigid section with respect to the second generally rigid section, with the restraint further configured to permit movement of the first generally rigid section with respect to the second generally rigid section when the annuloplasty ring is subjected to a dilation force. The restraint may be configured to permit rotational movement of the first generally rigid section with respect to the second generally rigid section when the annuloplasty ring is subjected to the dilation force. The restraint may comprise a lock configured to fail when the annuloplasty ring is subjected to a dilation force. The restraint may comprise suture, an elastic material or structure such as a spring, a plastically deformable material (including breakable materials), etc.

An annuloplasty ring according to an embodiment of the invention may include a movable connection between the first generally rigid section and the second generally rigid section, wherein the movable connection is configured to survive application of the dilatation force. The movable connection may comprise a hinge, a generally flexible material such as tether, etc.

In an embodiment of the invention, an annuloplasty ring has a generally non-circular shape and has a generally rigid portion defining at least half of the circumference of the generally non-circular shape, and the annuloplasty ring is configured to assume a generally circular shape when dilated by a balloon catheter. The annuloplasty ring may include plastically deformable materials configured to maintain the annuloplasty ring in the generally non-circular shape. The plastically deformable materials may be configured to break or otherwise plastically deform and no longer maintain the annuloplasty ring in the generally non-circular shape when subjected to a dilation force. The annuloplasty ring may form a continuous loop, and may include elastically deformable material configured to provide tension within the continuous loop.

A method for repairing a patient's heart function according to an embodiment of the invention can include: providing an annuloplasty ring having a generally non-circular configuration but configured to assume a generally circular configuration when subjected to a dilatational force; and implanting the annuloplasty ring in a heart valve annulus. The method may also include deploying an expandable prosthetic heart valve within the annuloplasty ring and heart valve annulus. Deploying the expandable prosthetic heart valve within the annuloplasty ring and heart valve annulus may include dilating the annuloplasty ring to cause the annuloplasty ring to assume a generally circular shape.

The generally non-circular configuration of the ring may be a "D"—or kidney-shape, so-called dog-bone shape, etc.

Dilating an annuloplasty ring may include using a dilation balloon, such as the type currently used for dilation of native heart valves, which can be advanced within the annuloplasty ring and expanded to a desired pressure and/or diameter. As a general rule, dilation balloons used for dilation of native valves are formed from generally inelastic material to provide a generally fixed (i.e., pre-set) outer diameter when inflated. Once such balloons are inflated to their full fixed diameter, they will not appreciably expand further (prior to rupturing) even if additional volume/pressure is added therein. Typical pressures for inflating such balloons are between 1 and 6 atmospheres, with pre-set inflated outer diameters of such balloons being on the order of 18 to 33 millimeters. The dilation balloon may be expanded to a desired pressure (e.g., 1-6 atmospheres) sufficient to fully inflate the dilation balloon to its desired diameter and to dilate and expand the native valve and annuloplasty ring.

A typical rigid annuloplasty ring will withstand dilation pressures of several atmospheres such as provided by most dilation balloons without expanding and/or becoming elastic. By contrast, the annuloplasty ring of the current invention is configured to change shape and/or become expanded and/or generally elastic when subjected to sufficient pressure provided by a dilation balloon. If the dilation balloon is expanded, using sufficient pressure, to an expanded outer diameter larger than the inner diameter of the native valve and annuloplasty ring, the annuloplasty ring will expand in diameter and/or change shape and/or become elastic.

In one embodiment, the dilation balloon is configured with a pre-set inflated outer diameter which is larger, such as by 10-20% or more, than the inner diameter of the annuloplasty ring. As an example, if the annuloplasty ring of the invention has an inner diameter of 23 mm, a dilation balloon having an inflated diameter of 24-27 mm may be inflated within the annuloplasty ring to cause it to expand and/or become elastic.

Annuloplasty rings according to various embodiments of the invention can be configured to be generally rigid prior to dilation, but change shape and/or become expanded and/or elastic when subjected to a sufficient dilation pressure. For example, an annuloplasty ring could be configured to withstand naturally occurring dilation pressures that may occur during beating of the heart, but to become expanded and/or elastic when subjected to a desired pressure (e.g., from a dilation balloon), such as a pressure of 1 atmosphere, 2 atmospheres, 3 atmospheres, 4 atmospheres, 5 atmospheres, or 6 atmospheres, depending on the particular application.

Note that the dilation balloon inflated diameters and inflated pressures, as well as the pressures at which the annuloplasty ring of the invention would become expanded and/or elastic, set forth above are by way of example, and that the use of balloons with other pressures and diameters, and of annuloplasty rings configured to change shape and/or expand and/or become elastic when subjected to other pressures and expanded balloon diameters, are also within the scope of the invention.

A prosthetic heart valve is being developed having a structure that can expand and/or otherwise change configuration in order to accept a percutaneously-delivered prosthetic heart valve therein. Such a prosthetic heart valve is disclosed in U.S. patent application Ser. No. 12/234,559 filed concurrently herewith and entitled "Prosthetic Heart Valve Configured to Receive a Percutaneous Prosthetic Heart Valve Implantation," the entire contents of which are incorporated herein by reference.

BRIEF DESCRIPTION OF THE DRAWINGS

FIG. 6A depicts a prosthetic heart valve deployment catheter configured for annuloplasty ring dilation and prosthetic heart valve deployment according to an embodiment of the invention;

FIG. 6B depicts the prosthetic heart valve deployment catheter of FIG. 6A positioned within a heart valve annulus of a patient according to an embodiment of the invention;

FIG. 6C depicts the prosthetic heart valve deployment catheter of FIG. 6A dilating the annuloplasty ring and deploying the prosthetic heart valve according to an embodiment of the invention;

FIG. 6D depicts the prosthetic heart valve deployment catheter of FIG. 6A being withdrawn from the patient according to an embodiment of the invention;

FIG. 7A depicts a prosthetic heart valve deployment catheter configured for annuloplasty ring dilation and prosthetic heart valve deployment according to an embodiment of the invention;

FIG. 7B depicts the prosthetic heart valve deployment catheter of FIG. 7A with the proximal dilation balloon positioned within the heart valve annulus according to an embodiment of the invention;

FIG. 7C depicts the prosthetic heart valve deployment catheter of FIG. 7A dilating the annuloplasty ring according to an embodiment of the invention;

FIG. 7D depicts the prosthetic heart valve deployment catheter of FIG. 7A with the proximal dilation balloon deflated according to an embodiment of the invention;

DETAILED DESCRIPTION OF PREFERRED EMBODIMENTS

Figure 1:
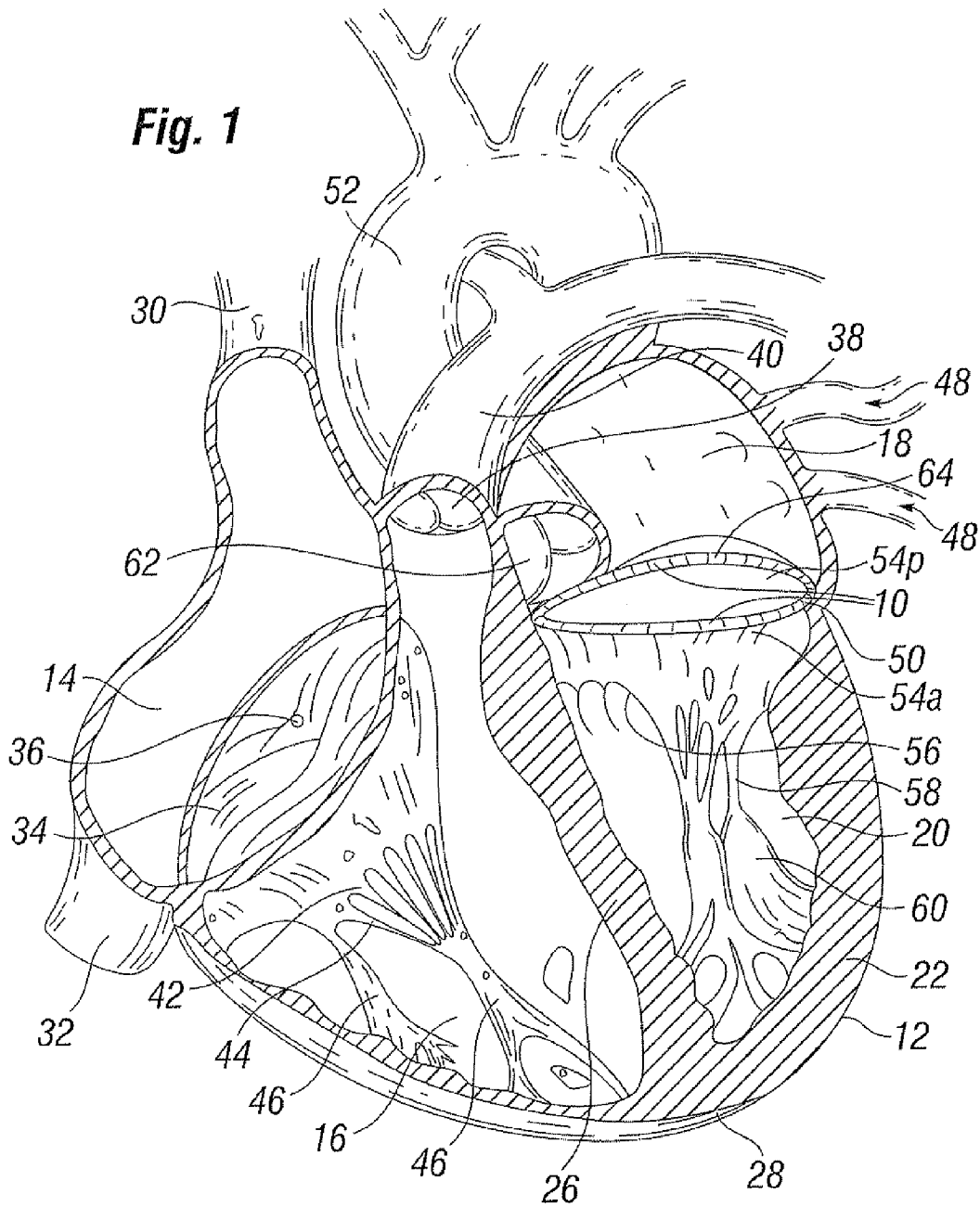
FIG. 1 depicts an annuloplasty ring deployed in a heart according to an embodiment of the invention.

With reference to FIG. 1, an annuloplasty ring device 10 according to the invention is depicted in a heart 12. The heart 12 has four chambers, known as the right atrium 14, right ventricle 16, left atrium 18, and left ventricle 20. The general anatomy of the heart 12, which is depicted as viewed from the front of a patient, will be described for background purposes. The heart 12 has a muscular outer wall 22, with an interatrial septum 24 (not visible in FIG. 1, but visible in FIG. 3b, etc.) dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendinae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve 50 controls blood flow between the left atrium 18 and the left ventricle 20. The mitral valve 50 is closed during ventricular systole when blood is ejected from the left ventricle 20 into the aorta 52. Thereafter, the mitral valve 50 is opened to refill the left ventricle 20 with blood from the left atrium 18. The mitral valve 50 has two leaflets (anterior leaflet 54a and posterior leaflet 54p), lower portions and free edges 56 of which are connected via mitral chordae tendinae 58 to papillary muscles 60 in the left ventricle 20 for controlling the movements of the mitral valve 50. Blood from the left ventricle 20 is pumped by power created from the musculature of the heart wall 22 and the muscular interventricular septum 26 through the aortic valve 62 into the aorta 52 which branches into arteries leading to all parts of the body.

In the particular embodiment depicted, the annuloplasty ring 10 is deployed in the mitral valve 50, and more particularly is secured (via, e.g., sutures) adjacent and around the mitral valve annulus 64. The annuloplasty ring 10 provides a desired shape to the mitral valve annulus 64, thereby providing proper alignment and closure of the mitral valve leaflets.

Figure 2A:
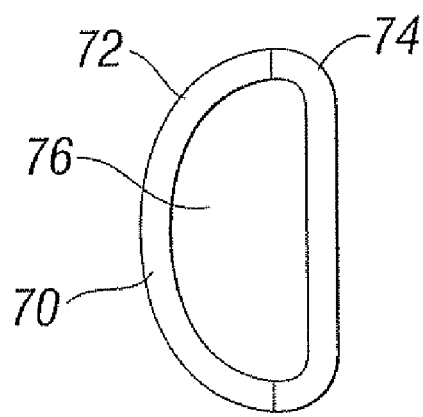
FIG. 2A depicts a top view of an annuloplasty ring according to an embodiment of the invention.

FIG. 2A depicts a top view of an annuloplasty ring 70 according to an embodiment of the invention, where the annuloplasty ring 10 is generally "D"-shaped and has a generally rigid portion 72 and generally flexible portion 74. In the particular embodiment depicted in FIG. 2A, the generally rigid portion 72 is generally curved, but the generally flexible portion 74 is generally straight.

Figure 2B:
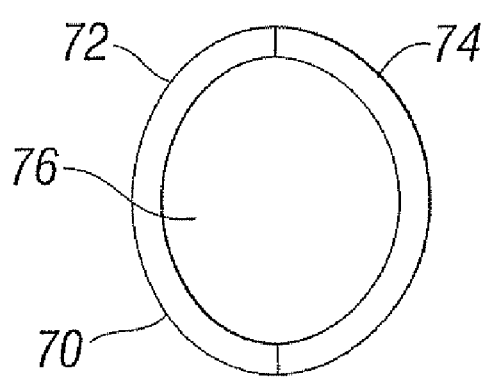
FIG. 2B depicts a top view of the annuloplasty ring of FIG. 2A after the annuloplasty ring has been dilated.

When the annuloplasty ring 70 of FIG. 2A is subjected to a dilation force (such as that from a dilation balloon), the annuloplasty ring 70 will transition from the generally "D"-shaped configuration of FIG. 2A to the generally circular shape of FIG. 2B. While the generally rigid portion 72 has remained generally unchanged in shaped (i.e., is still generally curved), the generally flexible portion 74 has transitioned from the generally straight configuration of FIG. 2A to the generally curved configuration of FIG. 2B. The overall result is that the "post-dilation" annuloplasty ring 70 of FIG. 2B has a generally circular opening 76 when viewed from the top.

Figure 3A:
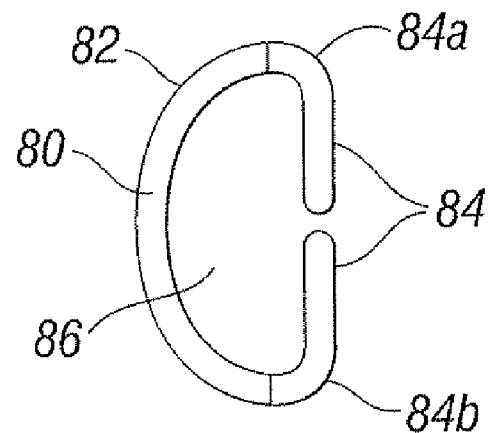
FIG. 3A depicts a top view of an annuloplasty ring according to a further embodiment of the invention.

FIG. 3A depicts a top view of an annuloplasty ring 80 according to a further embodiment of the invention, where the annuloplasty ring 80 is generally "D"-shaped and has a generally rigid portion 82 and a generally flexible portion 84 which has two separate generally flexible portions 84a, 84b. The annuloplasty ring 80 of FIG. 3A is accordingly discontinuous in structure (as opposed to the continuous structure of FIGS. 2A-2B). In the particular embodiment depicted in FIG. 3A, the generally rigid portion 82 is generally curved, but each of the generally flexible portions 84a, 84b are generally straight and are also generally aligned so that the generally flexible portion 84 is generally straight.

Figure 3B:
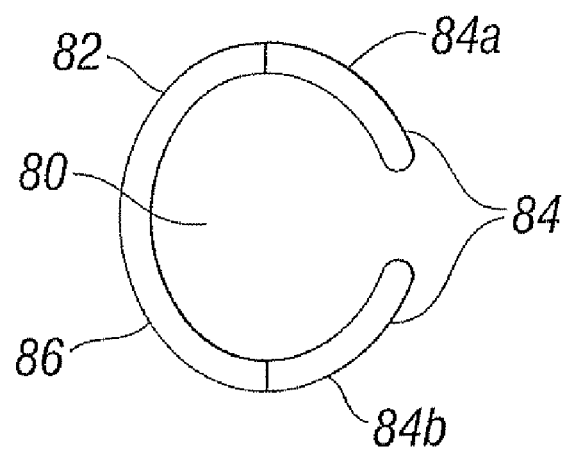
FIG. 3B depicts a top view of the annuloplasty ring of FIG. 3A after the annuloplasty ring has been dilated.

When the annuloplasty ring 80 of FIG. 3A is subjected to a dilation force (such as that from a dilation balloon), the annuloplasty ring 80 will transition from the generally "D"-shaped configuration of FIG. 3A to the generally circular (but still discontinuous) shape of FIG. 3B. While the generally rigid portion 82 has remained generally unchanged in shaped (i.e., is still generally curved), the generally flexible portions 84a, 84b have transitioned from the generally straight configurations of FIG. 3A to the generally curved configurations of FIG. 3B. The overall result is that the "post-dilation" annuloplasty ring 80 of FIG. 3B is generally circular but discontinuous when viewed from the top, providing a generally circular opening 86.

Figure 4A:
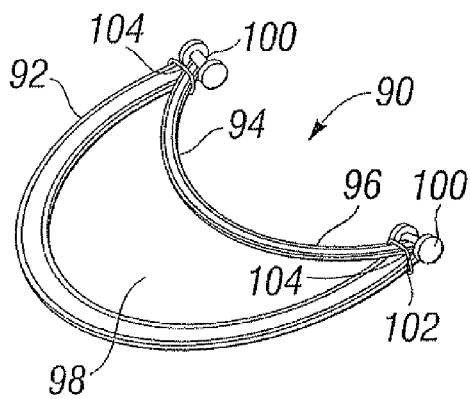
FIGS. 4A and 4B depict perspective and top views, respectively, of an annuloplasty ring according to a further embodiment of the invention.
Figure 4C:
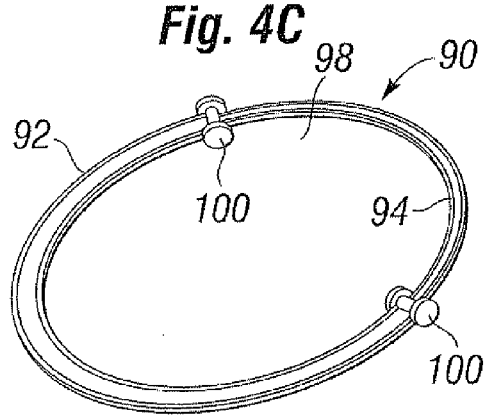
FIGS. 4C and 4D depict perspective and top views, respectively, of the annuloplasty ring of FIGS. 4A and 4B after the annuloplasty ring has been dilated.
Figure 4B:
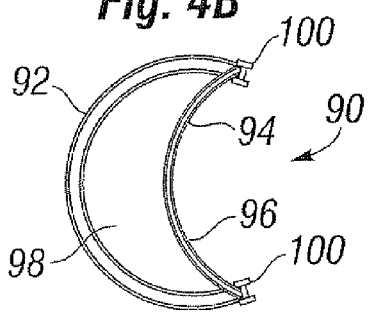
Figure 4D:
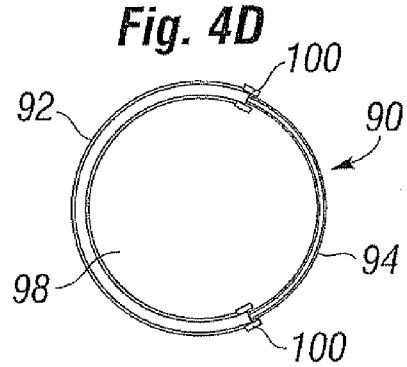

FIGS. 4A-4D depict a further embodiment of the invention, where an annuloplasty ring 90 has a first generally rigid portion 92 and second generally rigid portion 94. As depicted in FIGS. 4A-4B, the annuloplasty ring 90 in its pre-dilation configuration is generally D-shaped, with the second generally rigid portion 94 being shorter than the first generally rigid portion 92. The second generally rigid portion 92 defines a curve 96 which is directed inward with respect to the ring opening 98.

The first generally rigid portion 92 and second generally rigid portion 94 of the annuloplasty ring 90 are held together via a movable connection, which in the particular embodiment is formed by two hinges 100 secured to either end of the first generally rigid portion 92 and second generally rigid portion 94. The hinges 100 permit the second generally rigid portion 94 to rotate relative to the first generally rigid portion 92 when an outward force, such as that provided from an expanded dilation balloon, is applied to the annuloplasty ring 90. When the second generally rigid portion 94 is rotated relative to the first generally rigid portion 92 responsive to such an outward force, the annuloplasty ring 90 will transform from the generally D-shaped configuration of FIGS. 4A-4B to the generally circular configuration of FIGS. 4C-4D.

In order to prevent unwanted rotation of the second generally rigid portion 94 with respect to the first generally rigid portion 92, a lock or other restraint 102 is provided. The restraint 102 prevents rotation of the second generally rigid portion 94 with respect to the first generally rigid portion 92 prior to application of a dilatation force. However, the restraint 102 is configured to fail or open or otherwise release upon application of a significant dilation force (such as that provided by a dilation balloon) to permit movement (which in the particular embodiment depicted is in the form of rotation) of the second generally rigid section 94 with respect to the first generally rigid section 92 when the annuloplasty ring 90 is subjected to the dilation force.

In the particular embodiment of FIG. 4A, the restraint 102 comprises lines of suture 104 tied between the first generally rigid portion 92 and second generally rigid portion 94. Other types of restraints are also within the scope of the invention, including elastically deformable materials and/or structures such as springs, and plastically deformable materials (including breakable materials) such as suture, metals, plastics, etc.

Figure 5A:
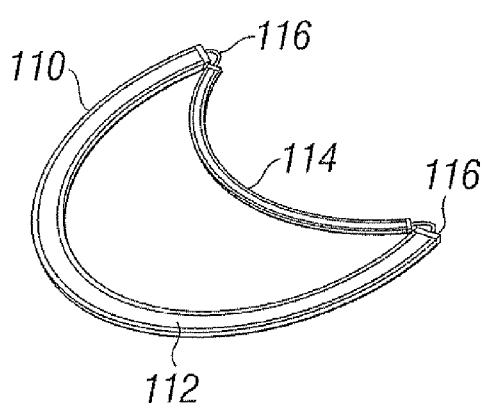
FIG. 5A depicts a perspective view of an annuloplasty ring according to a further embodiment of the invention.
Figure 5B:
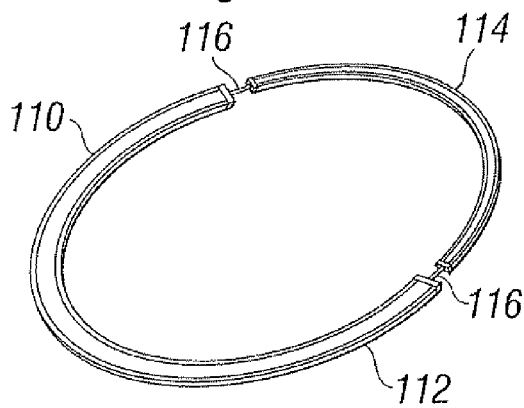
FIG. 5B depicts a perspective view of the annuloplasty ring of FIG. 5A after the annuloplasty ring has been dilated.

In a further embodiment of the invention depicted in FIGS. 5A-5B, the annuloplasty ring 110 has a restraint 116 that is a plastically deformable material (e.g., a bendable metal) that prevents relative movement/rotation of the two generally rigid sections 112, 114 prior to application of the dilation force, but upon application of the dilation force permits relative rotational or other movement while still providing a connection between the sections 112, 114. The restraint 116 may be a wire-like connection that can be bent to a desired shape in order to permit the two generally rigid sections 112, 114 to rotate relative to each other.

FIG. 6A depicts a prosthetic heart valve deployment catheter 120 configured for annuloplasty ring dilation and prosthetic heart valve deployment. The deployment catheter 120 has an elongated main body 122, a proximal end 124, and a distal end 126. The proximal end 124 includes a handle 128. The distal end 126 includes a dilation balloon 130 upon which an expandable prosthetic valve 132 is mounted. In the particular embodiment depicted, the prosthetic valve 132 includes a stent 134. The distal end 126 may also include one or more radiopaque markers 133 or similar visibility markers to improve visibility of the device within the patient when using fluoroscopy or other viewing technologies.

FIGS. 6B-6D depict deployment of a prosthetic heart valve 132 within a heart valve annulus 136 for a heart valve 138 where an annuloplasty ring 10 has previously been deployed. The annuloplasty ring 10 may have been deployed using any methods, including methods currently known in the art such as traditional (open chest) surgery, minimally-invasive (e.g., keyhole) surgery, and percutaneous surgery. The annuloplasty ring 10 encircles the heart valve 138. Depending on the particular application, the annuloplasty ring 10 can be deployed in the patient years prior to, days prior to, hours prior to, or immediately prior to deployment of the prosthetic heart valve 132 as depicted in FIGS. 6B-6D.

FIG. 6B depicts the prosthetic heart valve deployment catheter 120 of FIG. 6A with the distal end 126 advanced so that the dilation balloon 130 and expandable prosthetic heart valve 132 are positioned within the heart valve 138 in the patient's heart 140. The annuloplasty ring 10 is seen in cross-section, with a cross section of the ring first portion 10a at the right side of the valve annulus 136, and a cross section of the ring second portion 10b at the left side of the valve annulus 136. Note that the ring second portion 10b is depicted as extending somewhat more inward with respect to the valve annulus 134, which might be the case where the ring 10 is generally D-shaped and otherwise similar to that depicted in FIGS. 2A-2B and 4A-4C, with the ring first portion 10a corresponds to ring portions 72 (FIG. 2A), 92 (FIG. 4A), and the ring second portion 10b corresponds to ring portions 74 (FIG. 2A), 94 (FIG. 4A), respectively.

In the particular embodiment depicted in FIG. 6B, the deployment catheter 120 has been advanced over a guide wire 142, which was advanced into the patient's heart 140 and heart valve 138 prior to advancement of the deployment catheter 120 into the patient. Note that the use of a guide wire 142 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 6C, once the dilation balloon 130 and prosthetic heart valve 132 are properly positioned within the heart valve annulus 134, the dilation balloon 130 is expanded. The expanding dilation balloon 130 forces the stent 134 to expand outwardly, and crushes the native valve leaflets 144 against the heart valve annulus 136. The force from the expanding dilation balloon 130 dilates the heart valve annulus 136, and also forces the annuloplasty ring 10 to expand and/or assume a more circular shape, which in the particular embodiment depicted involves displacing the ring second portion 10b outward to a much greater extent than the outward movement of the ring first portion 10a.

In FIG. 6D, the dilation balloon 130 is deflated or otherwise reduced in diameter, with the prosthetic valve 132 deployed in the heart valve annulus 136 and held in place by the stent 134. The outward pressure from the expanded stent 132, along with the inward pressure from the heart valve annulus 136, from the now-crushed native valves 144, and/or from the now-dilated annuloplasty ring 10, combine to firmly seat the prosthetic valve 132 in the desired position in the heart valve annulus 136. The deployment catheter 120 with the dilation balloon 130 can then be withdrawn from the heart 140, leaving the prosthetic heart valve 132 in its deployed position in the patient.

In a further embodiment of the invention, the native heart valve 138 is dilated in a separate step from deployment of the prosthetic heart valve 132. FIG. 7A depicts a prosthetic heart valve deployment catheter 120 configured for annuloplasty ring dilation and prosthetic heart valve deployment using two separate balloons, and more specifically a distal balloon 130a and a proximal balloon 130b. The distal balloon 130a is configured to deploy the prosthetic valve 132, which is positioned on the distal balloon 130a, whereas the proximal balloon 130b is configured for dilation.

FIGS. 7B-7D depict dilation of the native valve 138, valve annulus 136, and annuloplasty ring 10 using the proximal balloon 130b. In FIG. 7B, the deployment catheter 120 has been advanced into the heart 130 with the distal balloon 130a (with prosthetic valve 132 thereon) advanced past the native heart valve 138, and the proximal balloon 130b positioned within the native heart valve 138 and valve annulus 136.

The proximal balloon 130b is inflated or otherwise expanded, as depicted in FIG. 7C, thereby dilating the native valve 138, valve annulus 136, and annuloplasty ring 10. The annuloplasty ring 10 is expanded and/or assumes a more circular form, similarly to the changes previously discussed with respect to the dilation discussed in FIG. 6C above.

After dilation of the native valve 138, the proximal balloon 130b is deflated or otherwise reduced in diameter, as depicted in FIG. 7D. The deployment catheter 120 may then be withdrawn from the patient until the proximal balloon 130b is proximal of the valve annulus 138 and the distal balloon 130a is positioned within the valve annulus 138. The distal balloon 130a will be positioned within the valve annulus 138 in a similar fashion to that depicted for balloon 130 in FIG. 6B. The distal balloon 130a will then be expanded to deploy the prosthetic valve 132 in essentially the same manner as was discussed and depicted in FIGS. 6B-6D. The distal balloon 130a will serve to deploy the prosthetic valve 132, and may also serve to further dilate the native valve native valve 138, valve annulus 136, and annuloplasty ring 10.

Note that the expandable prosthetic valve may be self-expanding, in which case the deployment catheter may not have a dilation balloon as depicted in FIGS. 6A-6D and 7A-7D. Moreover, such a self-expanding prosthetic heart valve could be deployed with or without prior dilation of the annuloplasty ring. For example, a self-expanding prosthetic heart valve may provide sufficient outward radial force to dilate the annuloplasty ring and/or to hold the now-dilated annuloplasty ring in an expanded configuration in order to provide sufficient room for the self-expanding prosthetic heart valve in it expanded configuration.

Figure 8A:
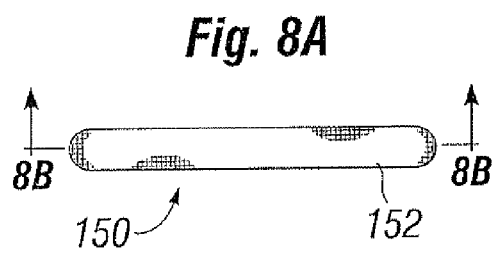
FIGS. 8A-8C depict side, top (in cross-section), and close-up sectional views, respectively, of an annuloplasty ring according to an embodiment of the invention.
Figure 8B:
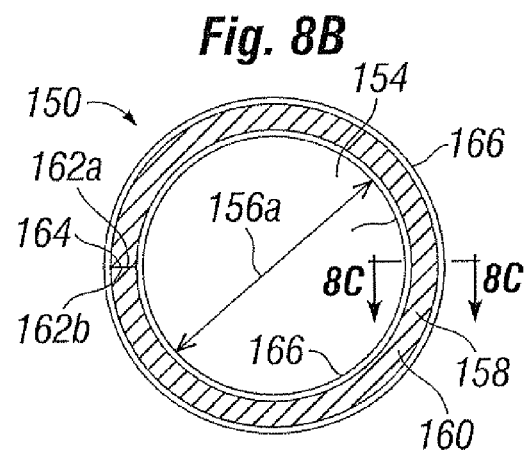
Figure 8C:
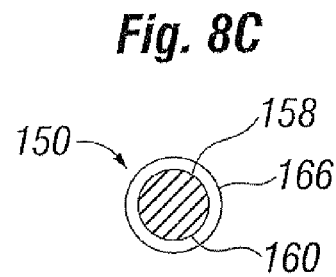

FIGS. 8A-8C depict an annuloplasty ring prosthetic heart valve 150 having a support frame 152 according to a further embodiment of the invention, with the annuloplasty ring 150 having an orifice 154 having an inner diameter 156a. The support frame 152 has a generally rigid and expansion-resistant core 158 formed from a single core element 160 which is bent or otherwise formed into a desired shape (which in the particular embodiment is generally circular) with opposing ends 162a, 162b meeting at a seam 164 so as to form the complete loop around the annuloplasty ring 150. The seam 164 may include adhesive, solder, welds, etc. in order to secure the two ends 162a, 162b together. The annuloplasty ring 150 includes a covering 166 around the support core 158. The covering 166 may be a cloth-like material, and may be a sewing ring configured to be sewn to the native heart valve annulus during deployment of the annuloplasty ring 150. The covering 166 is generally flexible, and may be generally elastic. The covering 166 (or a portion thereof) may also be generally compressible, especially in the portion facing inward toward the orifice 154, which can assist in seating an expandable valve therein. A compressible material may be applied onto or within the covering 166 in a position to provide a compressible region on the surface facing inward toward the orifice 154.

Figure 8D:
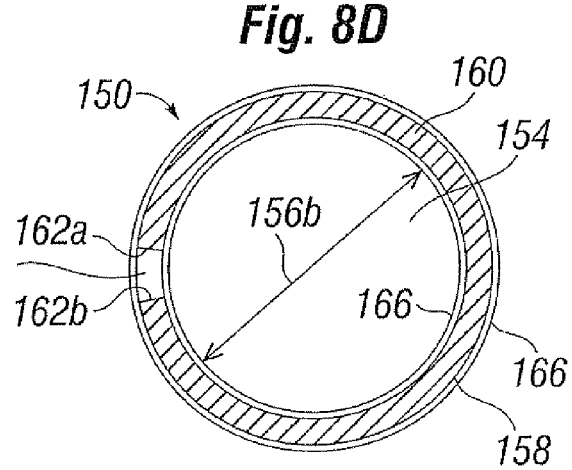
FIG. 8D depicts a top view, in cross-section, of the annuloplasty ring of FIGS. 8A-8C after the annuloplasty ring has been dilated.

When the annuloplasty ring 150 is subject to a dilation force such as that from a dilation balloon catheter, the support frame 152 will become non-rigid and expanded. More particularly, the seam 164 of the core 158 will rupture, so that the opposing ends 162a, 162b will be separated by an opening 168, and the core 158 will assume a generally C-shaped configuration as depicted in FIG. 8D. The covering 166 will stretch or otherwise expand circumferentially to accommodate the enlarged/expanded core 158, and the annuloplasty ring 150 will have an enlarged inner diameter 156b for the orifice 154. Depending on the particular embodiment, including the particular construction of the core 158 and/or covering 166, the (post-dilation) annuloplasty ring 150 may provide an inward (i.e., compressive) force toward the orifice 154. For example, the core 158 may be formed of a generally resilient spring-like material and/or memory material, and may be biased somewhat toward its non-dilated configuration (i.e., with the opposing ends 162a, 162b touching each other as in FIGS. 8A-8C). The covering 166 may also (or alternatively) be elastic and, after dilation of the annuloplasty ring 150, may provide an inward pull on the core 160 so as to bias the opposing ends 162a, 162b toward each other. This inward pressure can help to seat an expandable heart valve that may be deployed within the annuloplasty ring 150 and native heart valve. In an embodiment where compressible material is provided (e.g., as part of the covering 166) facing inward toward the orifice 154, then the compressible material can provide additional assistance in seating an expandable heart valve within the annuloplasty ring 150.

In some procedures where an expandable prosthetic heart valve is used to replace a native valve that has a previously-deployed annuloplasty ring, it may be desirable for the expandable prosthetic heart valve to have a deployed (expanded) orifice having a cross-sectional area approximately equal to the orifice cross-sectional area of the native valve. Such consistency between orifice areas can be useful in maintaining proper blood flow, so that the expandable prosthetic heart valve will provide the same blood flow as was provided by the native heart valve. For example, Edwards Lifesciences has Sapien™ expandable prosthetic heart valves having outer diameters of 23 and 26 mm, respectively, which have corresponding inner diameters of about 20 and 23 mm, respectively, which correspond to orifice areas of about 315 and 415 square mm, respectively. Accordingly, the post-dilation orifice area of the native valve orifice with annuloplasty ring may be on the order of 315 and 415 square mm (respectively) to accommodate such expandable prosthetic heart valves. In that several embodiments of annuloplasty rings herein are generally circular in shape after dilation, the post-dilation native valve orifice will generally be circular and require diameters of about 20 and 23 mm to accommodate the above-discussed Sapien™ expandable prosthetic heart valves. The dilated native valve orifice will generally be smaller than the dilated annuloplasty ring orifice area due to portions of the native valve (such as leaflets, etc) that can project inward of the annuloplasty ring.

In order to accommodate an expandable prosthetic heart valve, an annuloplasty ring according to some embodiments of the current invention will have a dilated inner orifice area that is larger by about 10%, 15%, 25%, 30%, or more than the pre-dilation inner orifice area. Where an annuloplasty ring is generally circular both prior to a after dilation, the annuloplasty ring post-dilation inner diameter may be larger by about 15%, 20%, 25%, 30%, 35%, or more than the pre-dilation inner diameter.

Note that the invention is not limited to the above differences between pre- and post-dilation inner diameters and/or orifice areas of the annuloplasty ring. For example, there may be applications where much smaller and/or much larger post-dilation inner diameters may be required. In some cases an expandable prosthetic heart valve will have an outer diameter only slightly larger than its inner diameter, so that less expansion of the native valve orifice (and accordingly of the annuloplasty ring) is required in order to accommodate the expandable prosthetic heart valve. In other cases an expandable prosthetic heart valve may have an outer diameter that is much larger than its inner diameter, so that a greater expansion of the native heart valve and associated annuloplasty ring is necessary to accommodate the expandable prosthetic heart valve. There may also be applications where it may be desirable to deploy an expandable prosthetic heart valve having a smaller or larger inner diameter than was provided by the native valve.

Figure 9A:
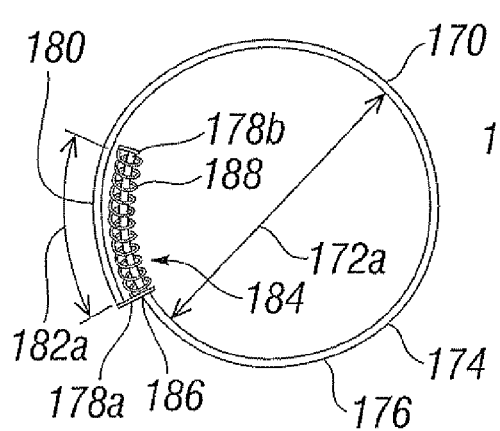
FIGS. 9A and 9B depict top views, in pre-dilation and post-dilation configurations, of an annuloplasty ring according to an embodiment of the invention.
Figure 9B:
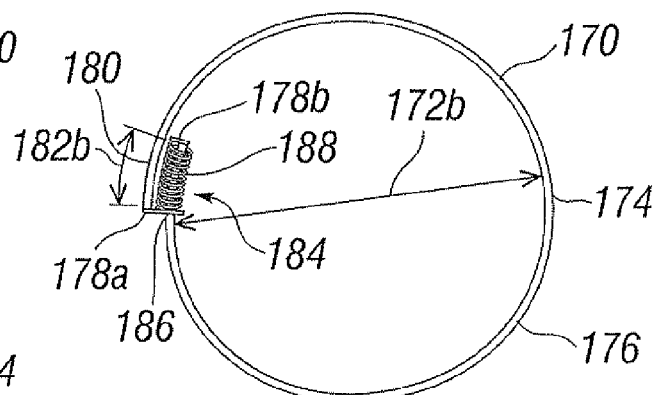

FIGS. 9A-9B depict a further embodiment of the invention, wherein a support frame 170 configured for use with an annuloplasty ring (such as the ring 150 in FIGS. 8A-8D) according to the invention. The particular support frame 170 is generally circular (although other shapes are within the scope of the invention) and defines an inner diameter 172a, and has a generally rigid core 174 formed from a single core element 176 which is bent or otherwise formed into a generally circular shape with opposing ends 178a, 178b which meet and connect at an overlapping section 180 having a length 182a. The overlapping section 180 may include adhesive, solder, welds, mechanical connections, ratchet-like assemblies, interacting portions, etc. in order to secure the overlapping ends 178a, 178b together. In the particular embodiment of FIGS. 9A-9B, the overlapping section 180 includes a sliding mechanical connection 184 having a slot 186 secured to one opposing end 178a, the second opposing end 178b having been passed through the slot 186 to form the overlapping section 180, and also including a spring 188 extending from the slot 186 to the second opposing end 178b. The spring 188 permits expansion and/or contraction of the support frame 170, with the spring 188 generally biasing the support frame 170 toward a smaller diameter, such as the smaller inner diameter 172a of FIG. 9A. The mechanical connection 184 also permits the support frame 170 to be expanded when subject to an outside force such as a dilation balloon and/or expandable prosthetic valve. When the support frame is expanded 170, the overlapping section 180 shortens to a smaller length 182b, and the inner diameter increases to a larger inner diameter 172b as depicted in FIG. 9B. Note that the spring 188 can also permit the support frame 1700 (and associated annuloplasty ring) to move with physiological annular dynamic motion, e.g., to make smaller expansions and/or contractions in response to normal valve function/heart movement as the patient's heart beats and pumps blood through the valve. The support frame 170 may include a covering (not shown) around the core 174, with the covering providing a surface through which suture can be passed to secure the annuloplasty ring to the native valve annulus. The support frame 170 may be formed of various materials, including elgiloy. The spring 188 can be configured to provide a specific force in opposing expansion of the support frame 170, and may be configured so that the force provided is insufficient to oppose the dilation force from a dilation balloon and/or expandable stent which might be expanded within the support frame 170. The spring 188 could be formed from traditional coil springs, compressible materials, pleated sewing rings, accordion sewing rings, and other configurations configured to provide a spring-like force.

Although a spring-like configuration that survives dilation is depicted in FIGS. 9A-9B, other embodiments are also within the scope of the invention. For example, a support structure may have overlapping portions having interacting portions that hold the overlapping portions together, but that will temporarily release their connection to permit the relative movement of the overlapping ends when subject to a dilation force, and then for the interacting portions to re-establish their connection once the dilation force is removed so that the support frame will again be generally rigid. Such an embodiment is generally rigid prior to dilation, becomes elastically expandable during dilation, and then becomes substantially rigid again after dilation. In a further embodiment, a support frame could be formed but with the interacting portions configured so that no fixed connection is formed between the overlapping ends after dilation, so that the support frame will be generally non-rigid after the dilation force has been applied. In such an embodiment, the support frame may be configured to provide (after dilation) an inward (compressive) force upon any expandable prosthetic valve that may be deployed within the annuloplasty ring. This inward compressive force may help to seat and otherwise hold the expandable prosthetic valve in its desired position within the native valve annulus and also within the now-dilated annuloplasty ring.

Figure 10A:
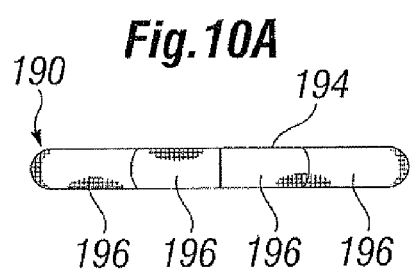
FIGS. 10A-10C depict top, side, and cross-sectional views, respectively, of an annuloplasty ring according to an embodiment of the invention.
Figure 10B:
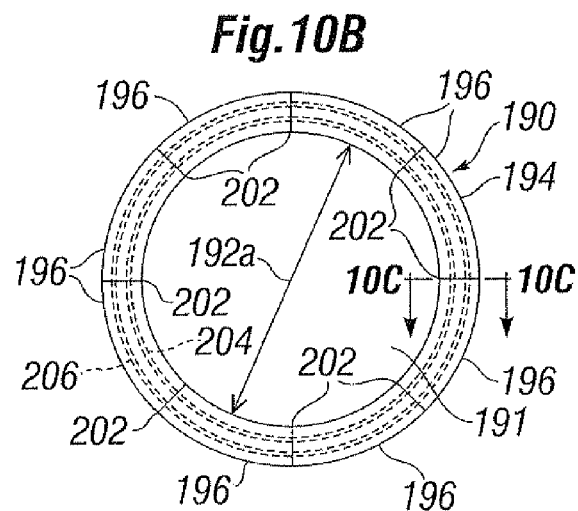
Figure 10C:
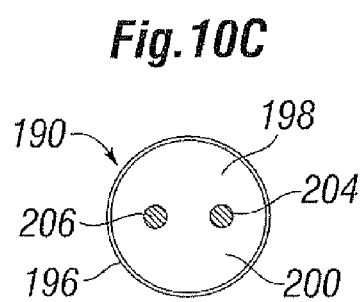

In another embodiment of the invention, an annuloplasty ring includes a support frame having a rigid and/or expansion-resistant core configured to separate into a plurality of pieces when subjected to a dilation force. Such a rigid and/or expansion-resistant core could be formed as a single piece, which might include one or more weak points that are subject to separation when subjected to a dilation force. In one embodiment a rigid and/or expansion-resistant core could be formed from a plurality of segments positioned in edge-to-edge fashion and configured to separate when subjected to a dilation force. FIGS. 10A-10C depict one such embodiment of a support frame 190 for use with a prosthetic heart valve according to the invention. The support frame 190 is generally circular (although other shapes are within the scope of the invention) and defines an orifice 191 having an inner diameter 192a, and has a generally rigid and/or expansion-resistant core 194 formed from multiple core segments 196 which are arranged in edge-to-edge fashion to form the generally circular shape of the core 194. Each segment 196 has an inner lumen 198, with the segments 196 when assembled into the core 194 forming a continuous core lumen 200.

Adjacent segments 196 join at seams 202, which may include adhesive, solder, welds, etc. in order to secure and/or seal the seam 202 between the adjacent segments 196. The support frame 190 has a pre-dilation cord 204 and a post-dilation cord 206 passing through the core lumen 200. The pre-dilation cord 204 may be a generally inelastic cord which is sufficiently tight to hold adjacent segments together and to prevent unwanted dilation of the support frame 190. A covering (not shown) may also be included to cover the core 194. The covering may be formed of cloth, and may be elastic.

Figure 10D:
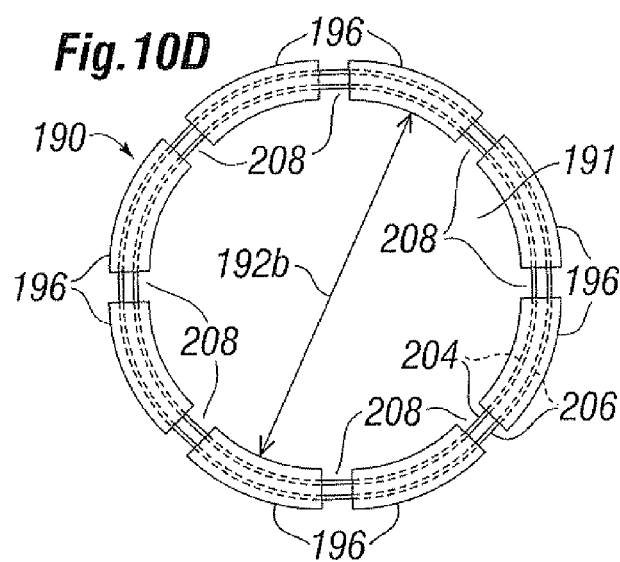
FIG. 10D depicts a top view, in expanded configuration, of the annuloplasty ring of FIGS. 10A-10C.

Both the seams 202 and pre-dilation cord 204 are configured to fail or stretch when subjected to a dilation force, such as that provided by a dilation balloon, whereupon the support frame 190 will assume the expanded configuration depicted in FIG. 10D, with an enlarged inner diameter 192b. For example, the pre-dilation cord 204 may be an inelastic cord configured to fail when subject to a selected force, such as 1, 2, 3, 4, or more atmospheres, which are within the range of forces provided by many dilation balloons used in percutaneously-deployed heart valve procedures. In one embodiment, the seams 202 are merely sealed, with the sealant providing little if any securement against separation of adjacent segments 196. In such an embodiment, the pre-dilation cord 204 may serve as the sole device to hold the core segments 196 together in the rigid and/or expansion-resistant (pre-dilation) configuration. Once the pre-dilation cord 204 fails or stretches due to the dilation pressure, essentially all of the seams 202 will separate so that adjacent segments 196 separate with spaces 208 separating the adjacent segments 196. The remaining portions of the pre-dilation cord 204 remain within the support frame 190 after dilation.

The post-dilation cord 206 remains intact after dilation and can serve to hold the support frame 190 together post-dilation. The post-dilation cord 206 could be elastic, and/or could be inelastic and have a larger diameter, and possibly a higher failure strength, than the pre-dilation cord 204. If the post-dilation cord 206 is elastic, it may provide an inward compressive force into the central orifice 191. If the post-dilation cord 206 is generally inelastic, it will remain intact after dilation either because its strength was too great to be ruptured by the dilation balloon or because it had a diameter that was larger than that of the inflated dilation balloon.

In a variation of the embodiment of FIGS. 10A-10D, the pre-dilation cord 204 could be left out of the support frame 190, and the seams 202 themselves could have adhesive or other connections that serve to hold the segments 196 together prior to dilation. In a further variation, the pre-dilation cord 194 could be left out of the support frame, with a post-dilation cord 206 configured to be elastic and with sufficient strength/elasticity to provide an inward compressive force into the central orifice with sufficient strength to hold the segments 196 together prior to dilation, but with the inward compressive force weak enough to permit the support frame 190 to be dilated and to permit an expandable prosthetic heart valve to be deployed therein. Accordingly, the post-dilation cord 206 would serve as both pre-dilation cord and post-dilation cord.

Visualization references may be included on or in various portions of the device according to various embodiments of the invention. For example, visualization references may be placed on, in, or adjacent the support frame 190, core 194, segments 196, pre-dilation cord 204, and/or post-dilation cord 206, etc. in the device of FIGS. 10A-10D. Such visualization references can help a user to properly position a dilation balloon and/or expandable prosthetic heart valve within the annuloplasty ring having the support frame 190. For example, visualization markers positioned at the generally rigid support frame 190 (or more specifically at the segments 196 and/or the pre-dilation cord 204 and/or post-dilation cord 206) could be used to guide delivery and expansion of a dilation balloon, and also to confirm that the support frame 190 and annuloplasty ring have been dilated. The visualization markers could also be used to guide delivery and expansion of the expandable prosthetic heart valve within the annuloplasty ring and support frame 190, and to confirm proper deployment of the expandable prosthetic heart valve.

Figure 10E:
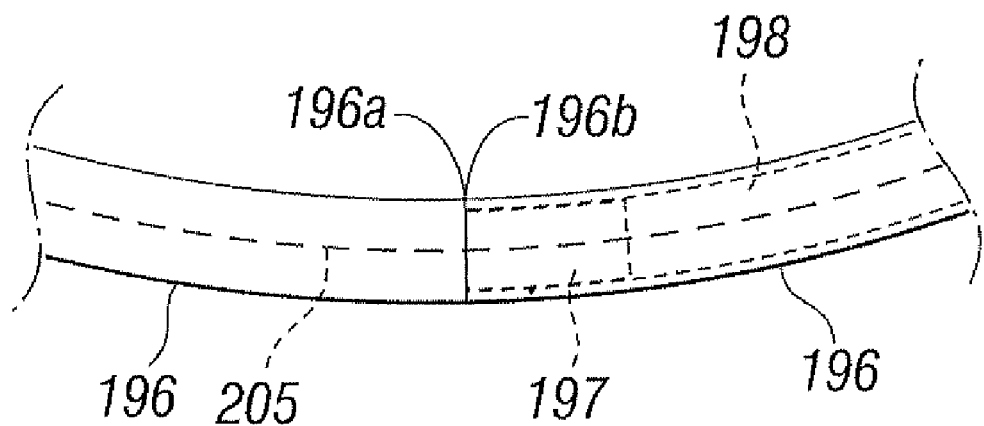
FIGS. 10E and 10F depict close-up top views, in undilated and dilated configurations, respectively, of an annuloplasty ring according to an embodiment of the invention.
Figure 10F:
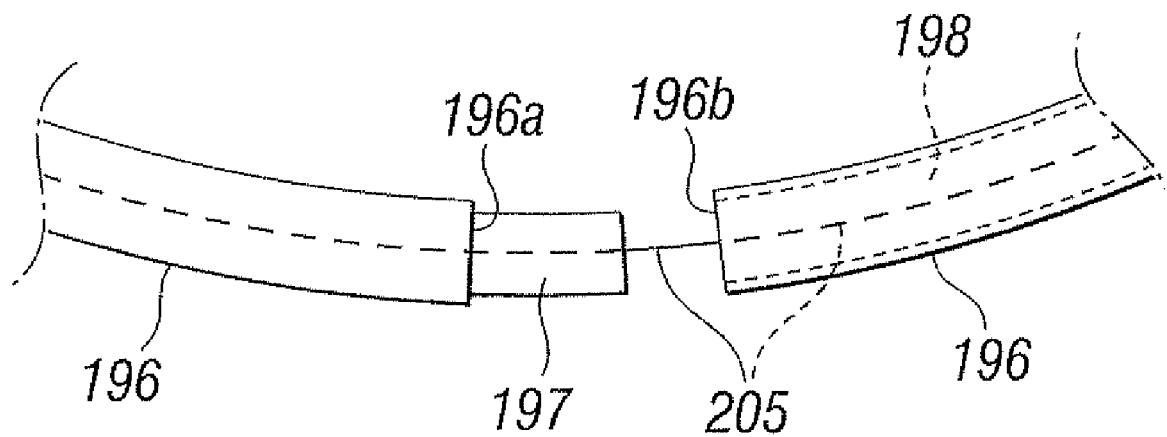

The support frame 190 may have segments 196 having ends 196a, 196b which interlock and/or otherwise interact in order to hold the segments 196 together and/or in alignment. As depicted in the close-up view of FIG. 10E, adjacent segments 196 may include interconnecting ends 196a, 196b, with one end 196a having a member 197 configured to be received within the lumen 198 or other opening in an end 196b of an adjacent segment 196. The interconnecting ends 196a, 196b keep the adjacent segments 196 in a desired alignment so that the segment ends 196a, 196b cannot slide sideways with respect to the member 197 and lumen 148, so that the general shape of the support frame 190 is maintained. The interconnecting ends 196a, 196b do permit the adjacent segments 196 to be pulled apart, as depicted in FIG. 10F, in order to permit expansion of the support frame 190 (as was depicted in FIG. 10D). The pulling apart of the segments 196 may be opposed by various structures set forth herein which oppose and/or restrict dilation of a support frame, such as one or more elastic and/or inelastic cords 205 configured to oppose and/or restrict dilation of the support frame 190 as was depicted in FIGS. 10A-10D.

Further embodiments of the invention may include an annuloplasty ring having a support frame including a core formed from segments connected end-to-end to form seams, with adjacent segments further connected via one or more individual inelastic and/or inelastic cords and elastic cords which extend only between adjacent segments. When the annuloplasty ring is subjected to a dilation force, the seams between the segments will fail and the support frame will separate into the individual segments 172. In one particular embodiment the inelastic cords do not serve to hold adjacent segments against each other, but instead permit adjacent segments to separate when subjected to a dilation force. The inelastic cords prevent excessive separation between any adjacent segments as the dilation balloon (or other dilation force) is applied, with the result being that the segments will all be spaced generally equally apart from each other once the full dilation force is applied. After the dilation force is removed, the elastic cords will serve to pull the adjacent segments toward each other and to provide a generally inward (compressive) pressure to the valve orifice while also permitting the post-dilation inner diameter of the annuloplasty ring to be a larger size than the pre-dilation diameter.

There are many variations of the above-cited embodiments, including various combinations of the various embodiments. For example, the pre-dilation cord 204 and/or post-dilation cord 206 of FIGS. 10A-10D could be used with the core 150 of FIGS. 8A-8D in order to provide inward compressive force after the core 150 was dilated. The post-dilation cord 206 of FIGS. 10A-10D could be replaced by a cover 158 such as that depicted in FIGS. 8A-8D, with the cover 158 serving to hold the post-dilation core assembly (including any segments and/or pieces thereof) together and also (if formed form elastic material) providing an inward compressive force to the orifice.

Note that, depending on the particular embodiment, an annuloplasty ring according to the invention may return to its pre-dilation inner diameter and/or shape after being subject to dilation such as from a balloon catheter. However, in such an embodiment, the balloon dilation will have rendered the "post-dilation" annuloplasty ring into a generally non-rigid and/or expansion-friendly configuration, such that a "post-dilation" annuloplasty ring will be forced with relative ease into a larger diameter and/or different shape when an expandable (e.g., balloon-expandable, self-expanding, etc.) prosthetic heart valve is deployed within the valve orifice of the native valve and annuloplasty ring.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A method of repairing a patient's heart function, comprising:

providing an annuloplasty ring having a first configuration having a first inner area but configured to assume a second configuration having a second inner area when subjected to a dilatational force, wherein in the first configuration the annuloplasty ring has a generally non-circular shape, in the second configuration the annuloplasty ring has a generally circular shape, and the second inner area is greater than the first inner area; and restoring the functionality of a native heart valve by implanting the annuloplasty ring in a heart valve annulus of the native heart valve, wherein the annuloplasty ring is implanted in the first configuration and the shape of the heart valve annulus is thereby remodeled to provide proper alignment and closure of the native heart valve leaflets;

and deploying an expandable prosthetic heart valve within the annuloplasty ring and heart valve annulus;

wherein deploying the expandable prosthetic heart valve within the annuloplasty ring and heart valve annulus further comprises: dilating the annuloplasty ring to transform the annuloplasty ring from the first configuration to the second configuration, to dilate the heart valve annulus.

2. The method of claim 1, wherein
the step of dilating the annuloplasty ring further comprises crushing the native leaflets against the heart valve annulus.

3. The method of claim 1, comprising, prior to the step of deploying the expandable prosthetic heart valve, the further steps of:

providing the expandable prosthetic heart valve on an inflatable balloon of a dilation catheter; and advancing the inflatable balloon with expandable prosthetic heart valve thereon into the heart valve annulus;

wherein deploying the expandable prosthetic heart valve comprises inflating the inflatable balloon to a pressure sufficient to dilate the annuloplasty ring from the first configuration to the second configuration, to dilate the heart valve annulus, to crush the native valve leaflets against the heart valve annulus, and to expand the expandable prosthetic heart valve.

4. The method of claim 3, wherein inflating the inflatable balloon to a pressure sufficient to dilate the annuloplasty ring comprises inflating the balloon to a pressure of no more than 6 atmospheres.

5. The method of claim 4, wherein inflating the inflatable balloon to a pressure sufficient to dilate the annuloplasty ring comprises inflating the balloon to a pressure of no more than 4 atmospheres.

6. The method of claim 1, further comprising:
dilating the annuloplasty ring to transform the annuloplasty ring from the first configuration to the second configuration and to dilate the heart valve annulus.

7. The method of claim 6, wherein dilating the annuloplasty ring further comprises crushing the native leaflets against the heart valve annulus.

8. The method of claim 6, wherein dilating the annuloplasty ring comprises expanding an inflatable balloon to a pressure of no more than 6 atmospheres.

9. A method for modifying a native heart valve, comprising:

providing an annuloplasty ring having a first substantially rigid configuration having a substantially non-circular shape and a second substantially non-rigid configuration having a substantially circular shape;

repairing the functionality of the native heart valve by implanting the annuloplasty ring into a valve annulus of the native heart valve with the annuloplasty ring in the first substantially rigid configuration, wherein after implantation the annuloplasty ring is in the first generally rigid configuration and whereby the shape of the heart valve annulus is thereby remodeled to provide proper alignment and closure of the native heart valve leaflets;

and after repairing the functionality of the native heart valve, dilating the annuloplasty ring and valve annulus and crushing the native heart valve leaflets against the valve annulus;

wherein dilating the annuloplasty ring and valve annulus and crushing the native heart valve leaflets against the valve annulus comprises deploying an expandable prosthetic valve within the valve annulus.

10. The method of claim 9, wherein dilating the annuloplasty ring comprises transforming the annuloplasty ring from the first substantially rigid configuration to the second substantially non-rigid configuration.

11. The method of claim 9, wherein the expandable prosthetic valve is a balloon-expandable prosthetic valve mounted on an expandable balloon, and wherein dilating the expandable prosthetic valve within the valve annulus comprises inflating the expandable balloon within the valve annulus to dilate the expandable prosthetic valve while simultaneously dilating the annuloplasty ring and transforming the annuloplasty ring from the first substantially rigid configuration to the second substantially non-rigid configuration.

12. The method of claim 11, wherein repairing the functionality of the native heart valve by implanting the annuloplasty ring into a valve annulus of the native heart valve comprises implanting the annuloplasty ring using an open chest surgical or keyhole minimally-invasive procedure, and wherein dilating the annuloplasty ring and valve annulus and crushing the native heart valve leaflets against the valve annulus comprises advancing the expandable balloon into the valve annulus via a percutaneous route.

13. The method of claim 9, wherein repairing the functionality of the native heart valve by implanting the annuloplasty ring into a valve annulus of a native heart valve comprises implanting the annuloplasty ring using an open chest surgical or keyhole minimally-invasive procedure.

14. A method of repairing a human heart in the body of a patient, comprising:

repairing functionality of a native mitral valve by surgically implanting a substantially D-shaped annuloplasty ring within the valve annulus of the native mitral valve to thereby remodel the valve annulus to a desired substantially non-circular configuration to provide proper alignment and closure of the native heart valve leaflets; and after repairing functionality of the native mitral valve by surgically implanting the substantially D-shaped annuloplasty ring, dilating the native mitral valve to permanently permanently transform the annuloplasty ring into a substantially circular shape and substantially non-rigid configuration and to remodel the valve annulus into a substantially circular configuration;

and implanting an expandable prosthetic heart valve within the valve annulus.

15. The method of claim 14, further comprising:
advancing a dilation balloon into the native mitral valve;
and wherein dilating the native mitral valve comprises inflating the dilation balloon to a pressure of 1 to 6 atmospheres.

16. The method of claim 15, wherein the expandable prosthetic heart valve is positioned on the dilation balloon, wherein dilating the native mitral valve further comprises deploying the expandable prosthetic heart valve within the valve annulus.

17. The method of claim 16, wherein advancing the dilation balloon comprises advancing the dilation balloon to the native mitral via the femoral artery in a percutaneous approach, the method further comprising:
after dilating the native mitral valve, removing the dilation balloon from the body of the patient, whereby the expandable prosthetic heart valve remains within the valve annulus and the valve annulus remains in the substantially circular configuration.

18. The method of claim 14, wherein the valve annulus has a pre-dilation inner orifice area and a post-dilation inner orifice area, and wherein dilating the native mitral valve comprises remodeling the valve annulus into a substantially circular configuration wherein the post-dilation inner orifice area is at least 15% larger than the pre-dilation inner orifice area.

* * * * *